United States Patent [19]

Averette

[11] Patent Number: 4,624,148

[45] Date of Patent: Nov. 25, 1986

[54] AUTOMATIC FLUID INJECTOR

[75] Inventor: Julius P. Averette, Baker, La.

[73] Assignee: Dynatech Precision Sampling Corporation, Baton Rouge, La.

[21] Appl. No.: 778,194

[22] Filed: Sep. 20, 1985

[51] Int. Cl.$^4$ ............................................. G01N 35/06
[52] U.S. Cl. ................................................. 73/864.21
[58] Field of Search ........... 73/864.81, 864.82, 864.21, 73/864.24, 864.22, 863.81

[56] References Cited

U.S. PATENT DOCUMENTS

| | | | |
|---|---|---|---|
| 3,266,322 | 8/1966 | Negersmith et al. | 73/864.22 |
| 3,912,456 | 10/1975 | Young | 73/864.22 |
| 3,960,020 | 6/1976 | Gordon et al. | 73/864.22 |
| 4,044,616 | 8/1977 | Harris, Sr. et al. | 73/863.81 |
| 4,478,095 | 10/1984 | Bradley et al. | 73/864.21 |

*Primary Examiner*—Stewart J. Levy
*Assistant Examiner*—Robert R. Raevis
*Attorney, Agent, or Firm*—Llewellyn A. Proctor

[57] ABSTRACT

An apparatus, viz. an automatic fluid injector, useful for the injection of very small, accurately measured quantities of fluid specimens into various media, e.g., the inlets of modern analytical instruments. The improved apparatus combination embodies an injector feed assembly wherein the probe sub-assembly comprises the combination of (i) an outer rigid tubular needle of relatively large inside diameter, and (ii) an inner flexible tubular needle, one terminal end of which is concentrically contained within said outer rigid tubular needle and of sufficiently small outside diameter to form an annulus between the external surface of said inner flexible tubular needle and the internal surface of said outer rigid tubular needle, while the opposite end of said inner flexible tubular needle is communicated with the barrel of said syringe. The outer rigid tubular needle protects the inner flexible needle on thrust of the probe sub-assembly through the septum of a fluid specimen-containing vial. Thereafter, a terminal end of the inner flexible tubular needle can be moved, or thrust from within the protective interior to the outside of said outer rigid tubular needle, and extended to the very bottom of a fluid specimen-containing vial carried by the magazine such that essentially all of the fluid specimen can be removed from the vial, picked up by the probe sub-assembly, and delivered to the barrel of the syringe for injection.

10 Claims, 7 Drawing Figures

AUTOMATIC FLUID INJECTOR

FIELD OF THE INVENTION

This invention relates to improvements in automatic fluid injectors, or automated syringes useful for automatically injecting very small, accurately measured quantities of a fluid into various media, e.g. the inlets of modern analytical instruments such as mass spectrographs or gas chromatographs.

BACKGROUND AND PROBLEMS

Automated fluid injection devices, particularly automated needle syringes, have gained wide acceptance by industry, universities, and by the scientific and medical communities. This is due in large part to the advantages offered by modern data gathering techniques, and consequent reduction in operating manpower without loss in accuracy.

Automated fluid injection devices of such character are capable of dispensing very small, accurately measured quantities of fluid specimens on the order of a few microliters, or very small fractions of a microliter, e.g. from about 0.01 to about 5 microliters, or fractional parts thereof. In the operation of such fluid injection devices, septum covered vials charged with portions of a fluid specimen are transported via a magazine to a station adjacent a probe assembly, the probe assembly picks up a specimen from a vial and a portion of the fluid specimen is conveyed via action of the probe assembly to the syringe. Within the barrel of the syringe, a quantity of the fluid specimen is measured out and injected via the dispensing end of the syringe into the inlet of the analytical instrument. Such a device is described, e.g., in U.S. Pat. No. 4,044,616.

Albeit very small quantities of fluid specimens can be measured out within the barrel of the syringe, and accurately injected, often hardly enough of a given total fluid specimen is available for such purpose. It is one thing to measure out and inject a given specific quantity of a fluid specimen into an analytical instrument, and it is another to effect virtually total delivery of a minimal available amount of a fluid specimen for such purpose. Unavoidably, a certain amount of the total of a given specimen never reaches the barrel of the syringe. Inevitably, it appears, a major portion of a given fluid specimen is left behind, and retained within a septum covered vial. Moreover, if there is an insufficient amount of the specimen available it may not be possible to pick it up from the vial in the first place. Present day automatic fluid injectors, notably the probe assemblies of such instruments are simply unable to pick up and deliver every last bit of the fluid specimen from the vial. Nor, where there is an insufficient amount of the specimen available, is it possible to pick it up and deliver same to the syringe. This is particularly unfortunate, for in many scientific and medical research situations only small, and infinitesmal quantities of a fluid specimen can be obtained from a source in the first place. There is thus a need for automatic fluid injeotors which are capable of picking up minute amounts of an available specimen, and for picking up greater amounts of the fluid specimens delivered by the septum covered vials for subsequent injection.

OBJECTS

It is a primary object of the present invention to satisfy these needs by providing a novel automatic fluid injector, particularly one having as part of its overall combination a probe assembly capable of withdrawing a small available quantity, as well as virtually the last residual increment of a fluid specimen from a filled septum covered vial of a transporting magazine for conveying same to the barrel of a syringe for dispensing to a given media.

A more specific object is to provide apparatus capable of continuously cyclically serially withdrawing virtually the last drop of a liquid specimen from prefilled septum covered vials, injecting the specimens in seriatim in accurately measured, infinitesmally small reproducible quantities, into a media, the apparatus being one which can be subsequently purged, cleaned and dried (e.g. washed with solvent and air dried) prior to the withdrawal and injection of a subsequent specimen to eliminate contamination of one specimen by another.

A further object is to provide apparatus of simple and relatively inexpensive construction, particularly apparatus which can be readily serviced and operated, which apparatus readily lends itself to rapid and mass production techniques.

SUMMARY OF THE INVENTION

These and other objects are achieved in accordance with the present invention which embodies improvements in fluid injector devices, notably automatic fluid injector systems which include the usual combination of (A) a syringe which contains a barrel into which a fluid specimen can be loaded, and means for the displacement of the fluid specimen from said barrel via a dispensing end thereof into a media, (B) an injector feed assembly comprised of a probe sub-assembly inclusive of a pair of concentrically mounted hollow needles for the pick-up of said fluid specimen for filling the barrel of said syringe, and (C) a magazine for transporting one or more fluid specimen-containing septum sealed vials for pick-up by the pair of hollow needles of said injector feed probe sub-assembly for delivery to the barrel of said syringe for subsequent injection into said media, e.g. the inlet of an analytical instrument. The apparatus combination of this invention embodies improvements in the injection feed assembly (B) wherein the probe sub-assembly comprises the combination of (i) an outer rigid tubular needle of relatively large inside diameter, and (ii) an inner flexible tubular needle, a terminal end and at least an adjacent portion thereof of which is contained within the base of said outer rigid tubular needle and is of sufficiently small outside diameter to form an annulus between the external surface of said inner flexible tubular needle and the internal surface of said outer rigid tubular needle, while the opposite end of said inner flexible tubular needle is communicated with the barrel of said syringe. The outer rigid tubular needle protects the inner flexible needle when the probe sub-assembly is thrust through the septum of a septum covered, fluid specimen-containing vial, and thereafter a terminal end of the inner flexible tubular needle can be moved, or thrust outside said protective outer rigid tubular needle and extended to the very bottom of a fluid specimen-containing vial (preferably, having a bottom of conical shape) carried by the magazine such that essentially all of tha fluid specimen can be removed from the vial, picked up by the probe sub-assembly, and delivered to the barrel of the syringe when the contents of the vial are pressurized by gas delivered from a source through the annulus to produce transport of fluid specimen from the vial through the probe sub-assembly to the barrel of the syringe.

In its more preferred aspects, the injector feed assembly (B), of the combination (A), (B), and (C), supra, includes a pair of telescoping frames, a first frame provided with a base, an opening through said base, a plurality of shafts, spaced apart and parallelly oriented one with respect to the other supported upon said base, and a second frame which carries said probe sub-assembly is provided with a plurality of openings corresponding in number and orientation with the shafts on the base of said first frame within which said shafts are guided and slidably mounted upon said first frame. A tubular barrel is mounted within and sealed inside said second frame, the central axis thereof being aligned upon the central axis of the opening within the base of said first frame. The outer rigid tubular needle of the probe sub-assembly, embodying the combination (i) and (ii), supra, is mounted and sealed within an end of the tubular barrel of said second frame, and the other end thereof is mounted within and reciprocably projectable through said opening within the base of said first frame when said second frame is telescoped upon said first frame. An end of the inner flexible tubular needle of the pair is extended through the outer hollow needle providing an annulus therebetween, projectable therefrom for extension into a vial in the manner suggested, and the opposite end thereof is communicated with the barrel of the syringe (A). A gas inlet to the tubular barrel is connected via said annulus with the interior of a septum covered vial on penetration of the septum by said outer rigid tubular needle, and the fluid-specimen contained in the vial is provided with a conduit to the barrel of the syringe when a terminal end of said flexible needle is projected therein. Thus, on the positioning by the magazine (C) of a septum covered fluid-containing vial beneath the probe sub-assembly the second frame can be partially telescoped upon said first frame to thrust the outer hollow rigid needle through the septum of a specimen sealed fluid specimen-containing vial, a terminal end of the inner hollow flexible needle can then be projected outside the protective outer rigid needle, thrust into and extended to the very bottom of the vial on further telescoping of said frames, the vial pressurized by gas injected via the gas inlet and passed via the annulus into the vial to pressurize same, such that essentially all of the fluid specimen can be removed from the vial, and delivered to the barrel of the syringe (A) via the inner flexible tubular needle of the probe assembly.

The injector feed assembly (B), in a yet more preferred embodiment, further includes means for purging, cleaning, and drying the instrument. All portions of the automatic fluid injector contacted by a fluid specimen, inclusive of the syringe, or syringe assembly, can be purged, and cleaned and dried (as with a solvent and air). The injector feed assembly (B) thus further specifically includes, as part and parcel of the combination, a probe seal assembly upon or adjacent which the base of said first frame of the injector feed assembly is affixed or located. The probe seal assembly comprises a valve body, preferably a tubular shaped body, containing a first opening, or lateral opening, extending through said valve body, this opening being in axial alignment with the opening in the base of said first frame and the septum of a septum sealed fluid specimen-containing vial transported by the magazine. The valve body also contains a second, or axial opening intersecting said first opening, this second opening extending through the valve body to a junction in the forward face of the valve body to which a drain line can be adjoined. A valve stem, preferably constituting a part of a cylinder-piston unit, is reciprocably mounted within said second, or axial opening, and an end of the stem provided with an opening comprised of axial and lateral segments. In a first position, the axial segments of the stem opening can be aligned within the annulus between the pair of needles of the probe assembly and upon a drain line such that a cleaning solvent, purge gas, or other drying gas, can be serially injected to clean said annular passageway and then withdrawn via said adjoined drain line. Additionally, cleaning solvent and purge gas are passed through the innerflexible needle of the probe assembly, and syringe to clean, purge, and dry said instrument. In a second position the stem can be withdrawn, and said second opening opened so that the probe can be projected through said first or lateral valve body opening into a fluid specimen-containing vial to effect pick up of fluid specimen from the vial carried by the magazine.

REFERENCE TO THE FIGURES

The characteristics of a preferred automatic fluid injector, and the principle of its operation, will be more fully understood by reference to the following detailed description of preferred embodiments, and to the attached drawings to which reference is made in the subsequent description. Similar numbers are used in the different figures to represent similar parts or components in different figures, and subscripts are used with numbers where there are duplicate components.

Figure 1A:
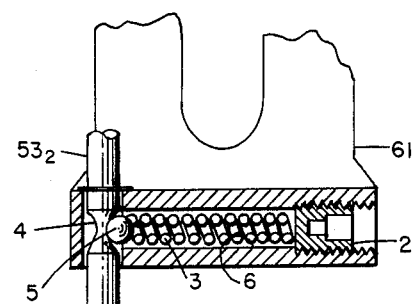
FIGS. 1A and 2A sub-features thereof.
Figure 1:
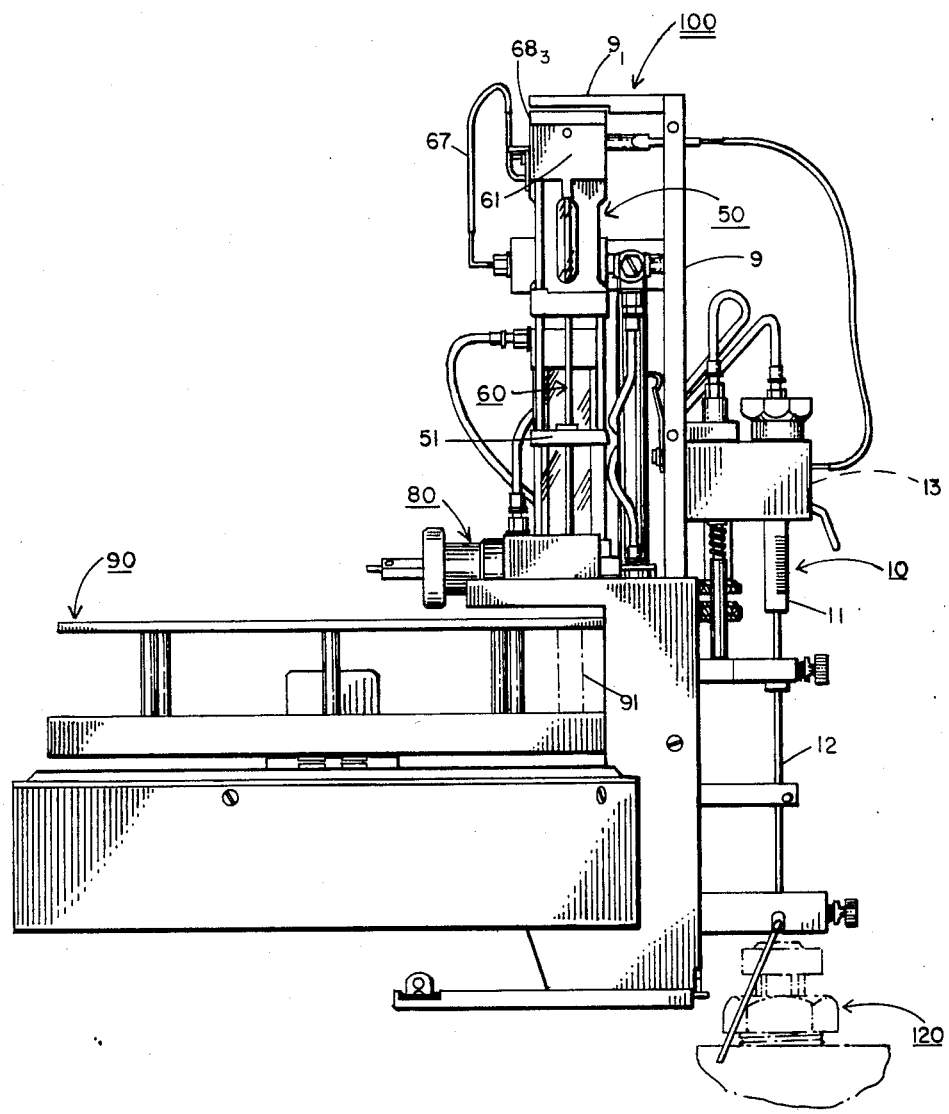
FIG. 1 depicts a side elevation view of a preferred automatic fluid injector wherein there is included a housing which contains (A) a syringe, or syringe assembly, (B) an injector feed unit, inclusive of its probe assembly, and valved probe seal sub-assembly, and (C) a carrousel type magazine.
Figure 2A:
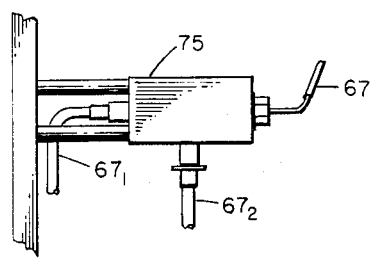
Figure 2:
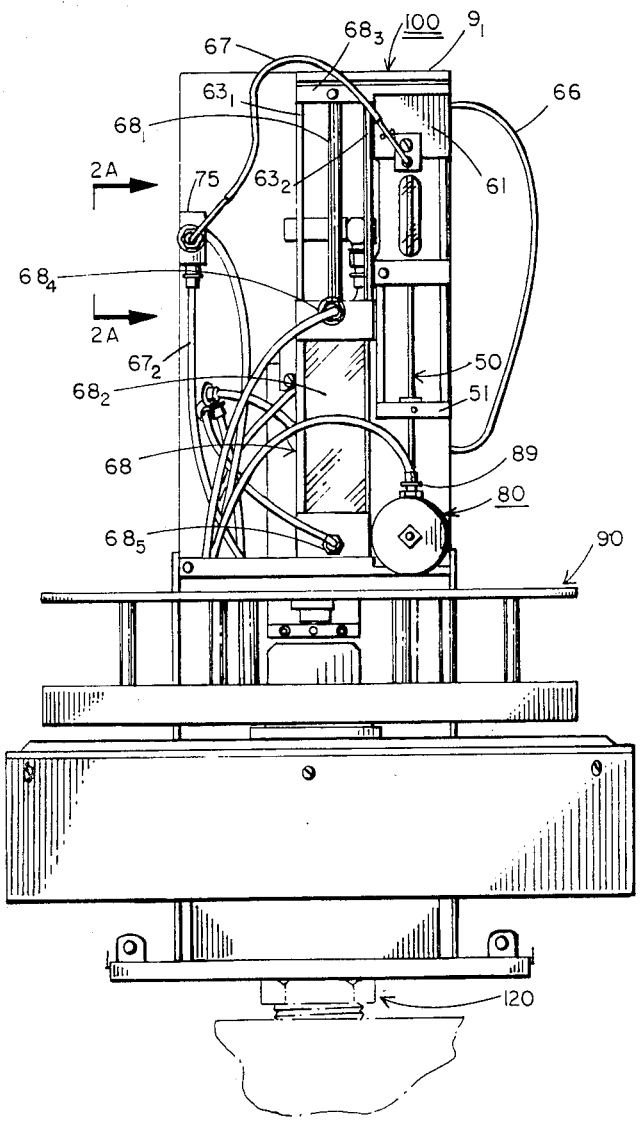
FIG. 2 depicts a front elevation view of the automatic fluid injector.
Figure 3:
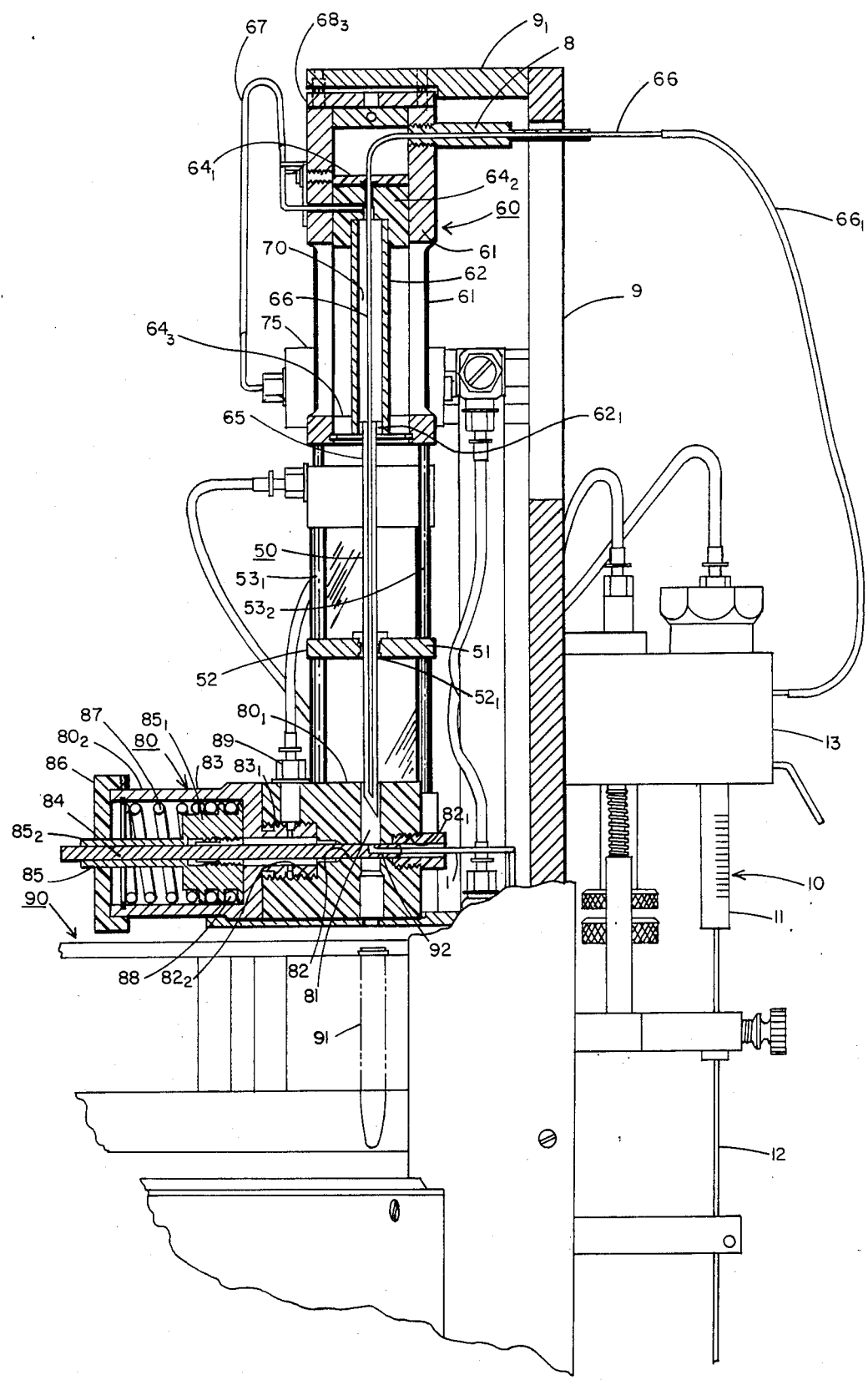
FIG. 3 depicts in partial section, a side elevation view of a major portion of the injector feed assembly, generally as shown in the preceding figures, notably FIG. 1, inclusive particularly of said pair of telescoping frames, probe sub-assembly, and valved probe seal assembly for use in serially purging, cleaning and drying said instrument between injections.
Figure 4:
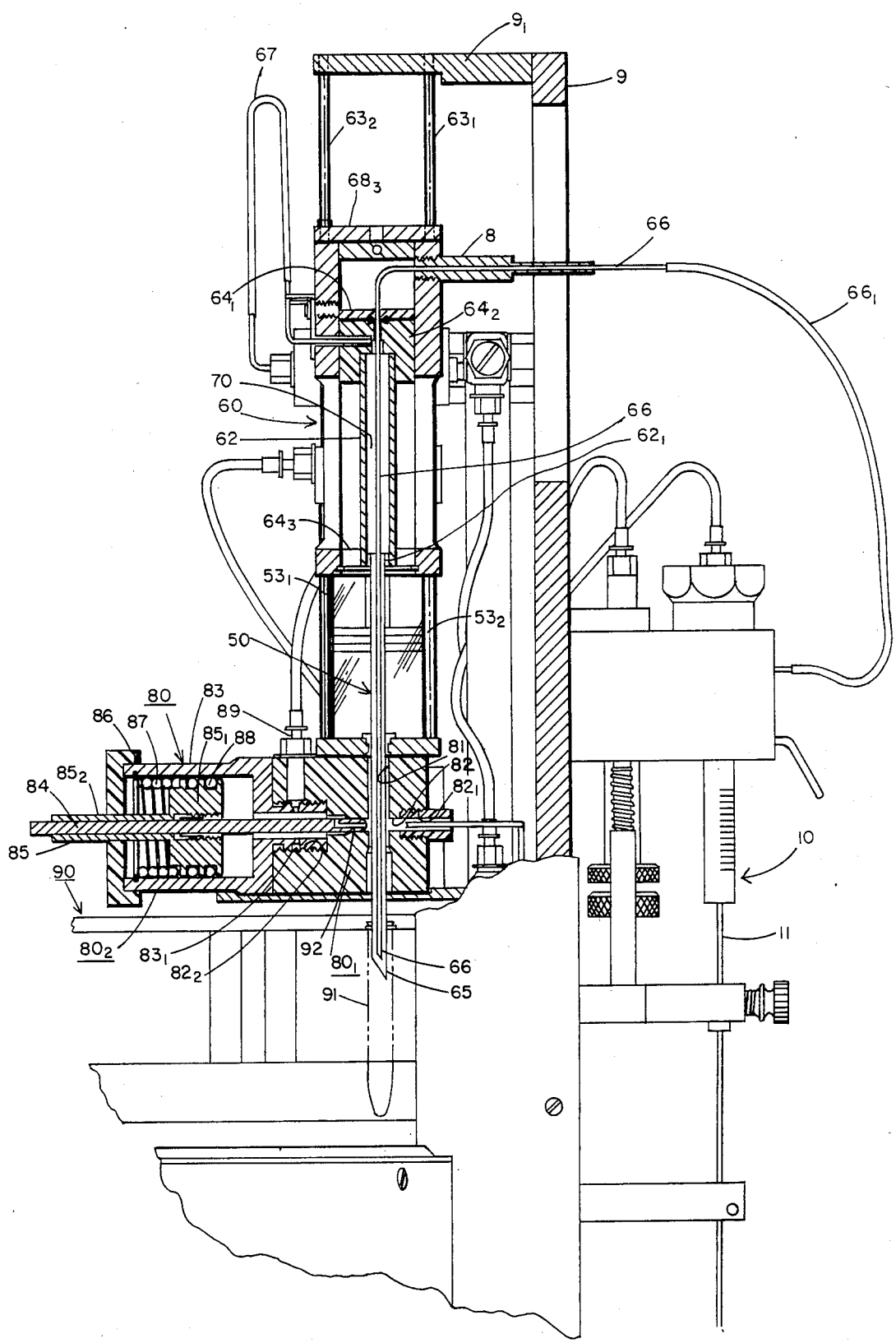
Figure 5:
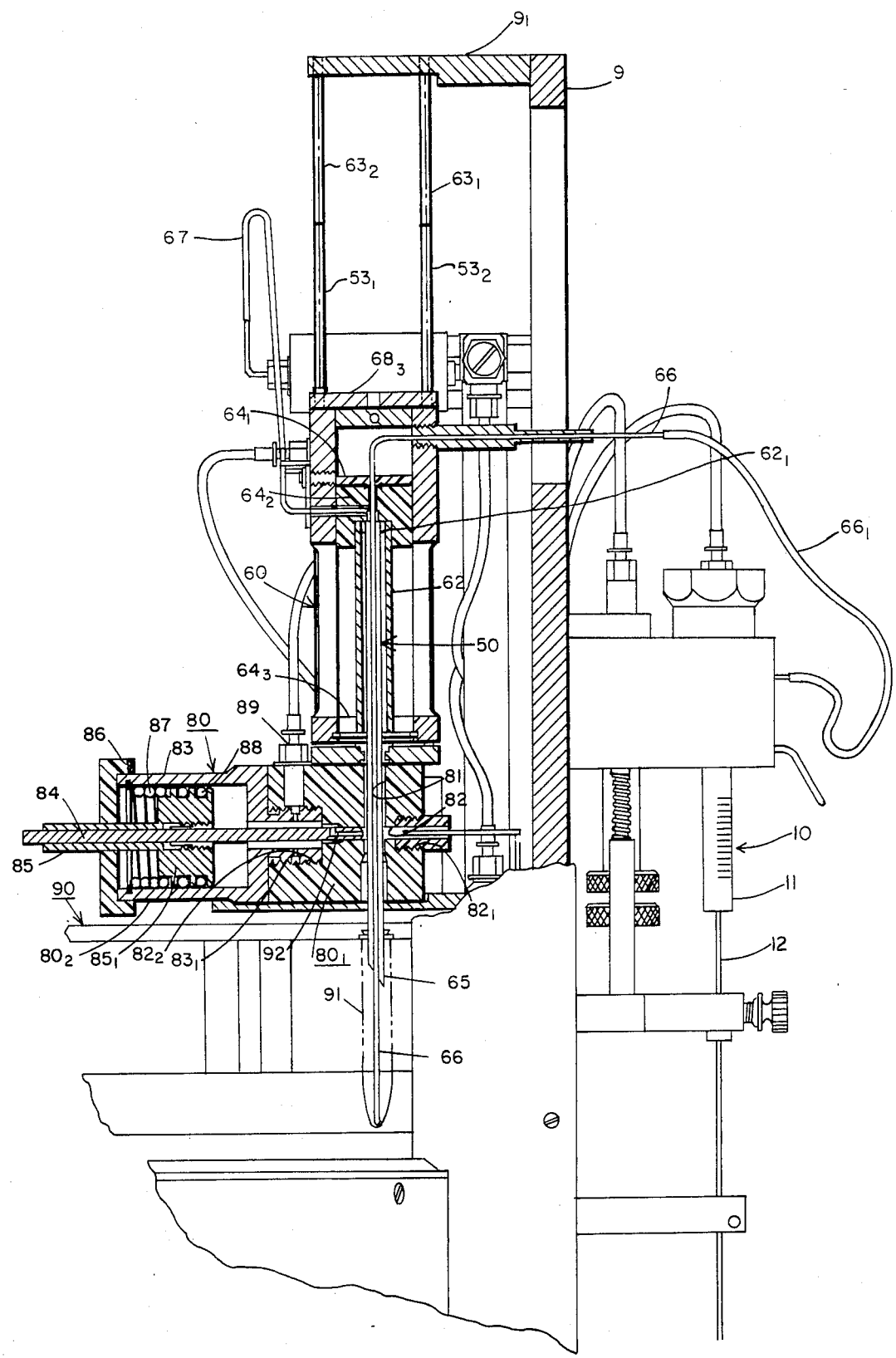

FIGS. 4 and 5, taken in sequence with the views covered by FIGS. 1–3, notably FIG. 3, depict the operation of the instrument in withdrawing a fluid specimen, and delivery of same to the syringe, or syringe assembly, for injection into the inlet of an analytical instrument.

DETAILED DESCRIPTION OF THE INVENTION

Referring to the figures, first generally to FIG. 1, there is shown a preferred type of automatic fluid injector 100. The principle sub-assemblies of the automatic fluid injector 100 include (A) a syringe, or syringe assembly 10, (B) an injector feed assembly 50, inclusive of a reciprocable probe assembly 60 which constitutes the primary contact device of this sub-assembly used for the pick up of a fluid specimen, and (C) a magazine or carrousel type feed tray 90 for transporting one or a plurality of vials of fluid specimens to the injector feed assembly 50 for pick up by probe assembly 60 for delivery to the syringe, or syringe sub-assembly 10. Accurately measured portions of the fluid specimens are injected into e.g., an inlet 120 of an analytical instrument, via the direct action of the syringe, or syringe sub-assembly 10. These several sub-assemblies (A), (B), and (C) are generally contained in whole or in part within a casing, or housing and are responsive to automatic control means such as described in U.S. Pat. No. 3,754,443. In brief compass, the principle features and overall function of these several sub-assemblies and their relation one to another are generally as follows;

(A) The syringe, or syringe sub-assembly 10, the principle purpose of which is to accurately measure out a preselected quantity of a fluid specimen for delivery to a media, or instrument, includes generally a syringe per se which is comprised generally of a barrel, plunger and a cannula, or hollow needle, mounted on the forward, or dispensing end of the barrel. In many syringes, or syringe assemblies, the plunger is withdrawn, the barrel of the syringe filled with a fluid specimen, and an accurately measured quantity of the fluid specimen injected by displacement on forward movement of the plunger. In other syringes, such as disclosed in U.S. Pat. No. 4,044,616, supra, the cannula, or needle itself is employed as the plunger. The barrel of the syringe is thus filled through a valved line, then the valve is closed, and the barrel moved relative to the needle (or needle relative to the barrel) to displace the fluid specimen from the barrel through the cannula, or needle. Any one of the syringes, or syringe assemblies, can be employed in the overall combination of this invention. A preferred type of syringe, or syringe assembly, is described by reference to said U.S. Pat. No. 4,044,616 by reference, e.g., to FIGS. 5-12, and the description associated therewith, herewith incorporated by reference and made part of the present disclosure.

With particular reference to FIG. 1, and/or FIGS. 3-5, it will thus be observed that a syringe assembly 10, includes the syringe per se comprised of a barrel 11, a cannula or hollow needle 12 sealed and slidably mounted within the forward end of the barrel 11, and valve 13 (not detailed) located at the rearward end of the barrel 11 for opening and closing the barrel 11 to the flow of the fluid specimen through the barrel 11 and hollow needle 12. On opening the valve 13 the fluid specimen can be flowed through the barrel 11 and needle 12 to purge and clean same and, on closing the valve 13 a measured amount of the fluid specimen can be delivered to and trapped inside the barrel 11 and needle 12 and then injected by relative forward movement of the barrel such that the needle 12 moves rearwardly into the barrel to displace and cause ejection of the fluid specimen through the dispensing end of the needle 12 after it is inserted into the septum inlet 120.

(B) The purpose of the injector feed assembly 50, inclusive of the probe assembly 60, is to pick up a fluid specimen from a septum covered vial 91 carried by the magazine, or carrousel feed tray 90, and convey the fluid specimen to the barrel 11 of the syringe 10. The injection feed assembly 50 includes a pair of upright telescoping frames 51, 61 slidably mounted upon vertical posts parallelly oriented with the wall 9 of the housing within which the various components are contained. The pair of telescoping frames include a first, or lower frame 51 provided with a base 52, a sealed central opening $52_1$ through said base 52, and a plurality of vertical posts, or shafts $53_1$, $53_2$ spaced apart, parallelly oriented one with respect to the other, and diagonally mounted upon two of the four corners of base 52. The second, or upper frame 61, which carries the probe aaaembIy 62, is slidably, and reciprocably mounted upon said first frame 51 via a plurality of elongate tubular openings which correspond in number and orientation with the number of posts, or shafts 53 of said first, or lower frame 51. The external diameter of the shafts 53 corresponds with the internal diameter of the openings, forming as it were a guide path, or track, such that the second, or upper frame 61 on descending can be telescoped upon the first, or lower frame 51. The telescoping frames 51, 61 are in turn reciprocably mounted upon the posts $63_1$, $63_2$ to which the frames 51, 61 are secured via member $68_3$ of the cylinder-piston unit 68 (FIG. 2).

The second, or upper frame 61 carries the pair of concentrically mounted hollow needles 65, 66 which constitute the very heart of the probe assembly 50 inclusive of a chamber 70 which can be pressurized after the needles 65, 66 of the probe assembly 50 are in place and inserted within a fluid specimen-containing septum covered vial 91 to convey said fluid specimen to the barrel of the syringe, or syringe assembly 10, as subsequently described. The second, or upper frame 61 is thus provided with a large internal opening of cylindrical shape formed by enclosing wall sections the upper end of which contains a pair of seals, an upper glandular ring seal $64_1$, and adjacent seal $64_2$, and the lower end of which contains an open-center nylon support ring, or washer ring $64_3$. The seals $64_1$, $64_2$ contain aligned openings through their central axis, and the bottom side of the upper lowermost seal $64_2$ is enlarged to accommodate an end of the tubular member 62 which is snugly fitted therein. The support ring $64_3$ likewise contains an opening through its central axis, and this opening is in alignment with the openings of seals $64_1$, $64_2$. The upper faced side of the opening of support ring $64_3$ moreover is enlarged to accommodate the lower end of the tubular member 62 which is snugly fitted therein. The inner lower end of the tubular member 62 is also provided with a tubular seal $62_1$ within the open center of which is contained an end of the rigid outer hollow needle 65 of the probe assembly 50. The inner flexible needle 66 of the probe assembly 50, it will be observed, is projected through the upper portion of wall 9 via a nozzle shaped member 8 which is threadably engaged to an internally threaded opening within an upper wall portion of the upper frame 61. The flexible needle 66 is bent and extended downwardly through the central openings of seals $64_1$, $64_2$ through chamber 70 of tubular member 62 and the outer rigid needle 65, the smaller diameter hollow needle 66 leaving an annular opening between the external wall thereof and the inside wall of the hollow needle 65 of the probe assembly 50. One terminal end of the inside, continuous flexible hollow needle 66 is directly connected via valve 13 to the valved side of the syringe, or syringe assembly 10, and the opposite terminal end thereof, in the position shown by reference to FIGS. 1-3 terminates short of, and is contained within the outer rigid hollow needle 65 of the probe assembly 50. A protective flexible tube $66_1$ through which a portion of the flexible hollow needle 66 is extended limits the flexing of said needle 66. The lower end of the hollow needle 65 of probe assembly 50, it will be further observed, extends into, and is aligned upon a lateral opening 81 of the valved probe assembly 80. The flexible needle 66, which is contained within said hollow rigid needle 65, can be extended as a unit through the probe seal assembly 80 via lateral opening 81 for picking up a fluid specimen from a septum covered vial delivered by the carrousel feed tray 90, e.g., vial 91. A pressurized gas from a suitable source can be delivered to the chamber 70, formed within tubular member 62, via line 67 and passed through the annulus between hollow needles 65, 66 as required in the operation of the probe assembly 50.

The probe assembly 50 is thus constituted principally of the combination of said outer rigid tubular needle 65 of relatively large inside diameter, and said inner flexible tubular needle 66 which is of sufficiently small outside diameter to form, with the inside diameter of the outer rigid needle 65 an annulus which extends the entire length of said outer rigid needle 65, forming a continuous conduit through the tubular barrel 62, or chamber 70, to the gas inlet 67. The hollow flexible needle 66, on the other hand, provides a continuous conduit from its lower terminal end back to the barrel 11 of the syringe 10. The inner flexible hollow needle 66 concentrically mounted, and shielded in this manner within the outer rigid hollow needle 65 is protected by the latter when the probe assembly 50 is thrust through the septum of a fluid specimen-containing vial, e.g., a vial 91 of conical shape with the tapered end directed downwardly. Thereafter, the inner hollow flexible needle 66 can be thrust outside said outer rigid tubular needle 65 and extended to the very bottom of a vial, e.g., the tapered bottom of vial 91 within which the liquid specimen is collected. In this manner, with the inner flexible needle 66 so extended, gas can be injected via the gas inlet 67, the tubular barrel 62 (or chamber 70) and the annulus to pressurize the contents of a vial such that essentially all of the fluid-specimen contained within the vial will be caused to flow through the flexible hollow needle 66 to fill the barrel 11 of the syringe 10.

The pair of telescoping frames 51, 61, also constituting a portion of the probe assembly 50, are actuated and moved downwardly and upwardly, or telescoped one upon the other in timed sequence to activate and reciprocate the probe assembly 50 for the pick up of fluid specimens from vials carried by the carrousel feed tray 90 for conveyance via the inner flexible needle 66 to the barrel 11 of the syringe 10 for injection into an inlet 120 in timed sequence.

The probe assembly 50 is reciprocated, upwardly and downwardly, via actuation of a double acting cylinder-piston unit 68 as best shown by reference to FIG. 2. The cylinder-piston unit 68 is constituted of a piston shaft, or piston $68_1$ the head of which is contained inside the cylinder portion of the unit, and the piston end of which extends outside the air tight chamber $68_2$. The piston shaft, or piston $68_1$ is operatively attached via the projecting element $68_3$ to the upper end of the upper, or second frame 61 of the probe assembly 60, and the element $68_3$ is slidably attached to the posts $63_1$, $63_2$. Whereas the cylinder-piston unit 68 may be actuated via various means, e.g., electrical or pneumatic, to reciprocate the frames 51, 61, it is preferably, as illustrated herein, pneumatically actuated. Thus, the cylinder-piston unit 68 is actuated and moved downwardly by the injection of pressurized air into the gas inlet $68_4$ at the top of the cylinder-piston unit 68 to telescope the pair of frames 51, 61, for withdrawal of a fluid specimen from a vial delivered by the carrousel tray 90 for transfer to the syringe assembly 10. Alternately gas is injected into the bottom of the cylinder-piston unit 68 via gas inlet $68_5$ to reposition the pair of frames 51, 61 to purge, clean and reset the probe assembly 50 for the continuance of another cycle of operation. Alternate injections of air into the inlets $68_4$, $68_5$ thus drives and reciprocates the frames 51, 61 in preselected sequence.

The function of the valved probe seal assembly 80 is to provide a valved sealed outlet, and guide means through which the hollow needles 65, 66 of the probe assembly 50 can be sequentially projected into septum sealed vials delivered by the carrousel feed tray 90 to a discharge station, or position of alignment with the lateral opening 81 of valved probe seal assembly 80 when the stem 84 of the valved portion of said probe seal assembly 80 is withdrawn, and the valve open as depicted by reference to FIGS. 4-5. The probe seal assembly 80 is constituted of two principal parts, a needle seal side, or portion $80_1$ of cylindrical or tubular shape which is provided with said lateral opening 81, and also includes a central axial opening 82 which intersects the lateral opening 81. The two opposite sides, or ends of valve portion $80_1$ which form the central opening 82 are tapped, enlarged and internally threaded: one tapped end $82_1$ providing an exit port for purge gases and liquids as hereinafter described, and the other $82_2$ a means for the threadable attachment for engagement thereto of the valved segment $80_2$. The valve segment $80_2$ of the probe seal assembly 80 is also of cylindrical, or tubular shape, and of external diameter corresponding substantially with that of seal segment $80_1$. The valved segment $80_2$ is constituted of a tubular body 83, a forward shank portion $83_1$ which is externally threaded and threadably engaged with the internally threaded opening $82_2$ of seal segment $80_1$. The opposite end of the seal segment $80_1$ is provided with an enlarged opening in axial alignment with that extending through the shank portion $83_1$ and therein is provided an actuable stem-piston assembly which includes a stem 84 which is set within a concentrically mounted piston 85, the latter including a relatively large diameter end $85_1$ (providing a piston head) and small diameter end $85_2$ (forming a piston shaft within which the stem 84 is concentrically mounted). The actuatable stem-piston unit is held in place within the enlarged opening via an open-centered end cap 86 and the stem-piston unit is biased in closed position (as shown in FIG. 3) via a tensioned helical shaped spring 87 which is seated between the rearward face of the piston head $85_1$, or large diameter end of the piston 85 and forward face of the cap 86. The stem-piston unit is sealed within the enlarged opening via a pair of o-rings 88 seated within a pair of concentric grooves located in the external face of the piston head $85_1$, or large diameter end of said stem-piston unit. The forward end of the stem 84, it will be observed, is provided with a continuous opening 92, inclusive of a lateral (or vertically oriented) segment which can be aligned and communicated with the lateral opening 81 of the valve probe seal assembly 80, and the lateral segment in turn intersects with an axial segment which is aligned upon the axial opening 82 of the valved probe seal assembly 80. The stem-piston unit in one position, i.e., that shown is by reference to FIGS. 1-3 physically blocks lateral opening 81 of the probe seal assembly 80 so that the hollow needles 65, 66 of the probe assembly 50 cannot pass, though fluid can be passed via lateral opening 81 and through the continuous opening 92 formed by the lateral and axial segments of said opening 92 as required in cleaning and purging the system. In its opposite position, as shown by FIGS.

4-5, such as occurs when pressurized gas is injected via line 89 into the valve interior to exert force on the large diameter end 85₁, or piston head 85₁, of the stem-piston unit to further compress helical spring 87, the stem 84 is retracted sufficiently that it is clear of the lateral opening 81 such that the hollow needles 65, 66 of the probe assembly 50 can be passed through the lateral opening 81 of the opened valve.

(C) The feed tray 90 whose function it is to transport fluid specimen filled vials to a location for pick up by the probe or probe assembly 50, can be of virtually any type, or design. For example, it can be of any one of several types, e.g., as described in U.S. Pat. Nos. 3,754,443, 3,824,859, 3,885,438 and 3,940,995. In a preferred embodiment, as described herein, a carrousel feed tray 90 is provided for conveying fluid specimen containing vials, preferably vials of conical shape, in seriatim to a location beneath the probe seal assembly 80 for pick up by needles 65, 66 of probe assembly 50. Suitably, the upper ends of the vials are sealed with an elastometer septum to prevent leakage and contamination, and permit pressurization. As the vials are moved into position beneath the probe assembly 50, the probe 50 is thrust downwardly so that the hollow needles 65, 66 pass through opening 81 of the probe seal assembly 80 (FIG. 4), the pointed or tapered end of outer rigid needle 65 penetrating the septum of a vial in an initial step in preparation for pick up and delivery of a fluid specimen to the syringe assembly 10. A preferred vial is one the bottom of which is tapered inwardly to provide a small volume into which the fluid specimen can be concentrated so that maximum amount of a fluid specimen can be withdrawn and taken by the flexible needle 66 for delivery to the syringe assembly.

An operating cycle is conveniently described principally by reference to FIGS. 3 through 5, these figures depicting the pick up of a fluid specimen from a septum covered vial and delivery thereof to a syringe, or syringe assembly 10, injection of a preselected quantity of the fluid specimen into the inlet of an analytical instrument, and the purging, cleaning and drying of the system as follows:

(a) Referring first to FIGS. 1-3, particularly FIG. 3, the clean, purged automatic fluid injector 100 is shown in ready position for the pick up of a fluid specimen from a septum covered vial 91 positioned by the carrousel feed tray 90 under opening 81 of the valved probe seal assembly 80 for such purpose. The forward end of the valve stem 84 of the valved probe seal assembly 80 is located in its extreme forward position, and hence covers and closes the opening 81. The terminal end of the outer, rigid hollow needle 65 of the probe assembly 50 rests snugly within the entry of the opening 81 just above the closed valve. The upper, or second frame 61 of the injector feed assembly 60 is at its maximum elevation with the upper base portion thereof, which is affixed to horizontal member 68₃, resting close to the horizontal segment 9₁ of the housing wall 9. At this point in time the terminal end of the inner flexible needle 66 is retracted inside the shielding outer rigid needle 65. The upper and lower frames 51, 61 of the feed assembly 60 are in an untelescoped position, one in relation to the other. Valve 13 of the syringe 10 is open. The barrel of the syringe 10 is ready for receipt of a fluid specimen, the syringe 10 is in raised position and the dispensing end of the needle 12 thereof is raised above, and clear of the septum inlet 120.

(b) Reference is made to FIG. 4. The stem 84 of the valved probe assembly 80 is retracted to uncover the opening 81 of said valved probe assembly 80. Pressurized gas is injected via gas inlet 68₄ of cylinder piston unit 68 (FIG. 2) which pushes the upper, or second frame 61 downwardly via withdrawal of the piston 68₁ of cylinder-piston unit 68 which exerts a downward force via the connecting member 68₃ against the upper platform portion of the frame 61 to partially telescope the upper frame 61 with the lower frame 51 of the injector feed assembly 60, as depicted by reference to FIG. 4. The outer, rigid hollow needle 65 of the probe assembly 50 moves downwardly and the tapered, or pointed end thereof pierces the septum of vial 91. There is no relative movement between the hollow needles 65, 66, the flexible hollow needle 66 remaining completely enclosed within, shielded and protected by the outer rigid hollow needle 65 of the probe assem 50.

At this point in time the frames 51, 61 of the probe assembly 50 move downwardly together in unison, these members being temporarily locked together via an inertia lock mechanism depicted by reference to FIG. 1A. One or both of the vertical posts 53₁, 53₂ is thus notched, or indented and the lower end, or base of the upper frame 61 is thus provided with one or two horizontally oriented openings within which is fitted a bearing-spring mechanism for temporarily locking the two frames together. Thus, the outwardly faced lower end of the base 61 within a vertical opening through which the vertical post 53₂ is passed is intersected by a tapped, internally threaded lateral, or horizontal opening 6. A ball bearing 5 is thrust within the notch 4 via a tensioned helical spring 3 seated between the bearing 5 and the externally threaded plug 2 threadably engaged with the tapped opening 6. The tensioned spring 6 acting upon the ball bearing 5 thus locks the frame 61 to the vertical post 53₂ until such time that the downward momentum of the frame 61 overcomes the tensioned spring 3 and forces the ball bearing 3 out of the notch 4 to uhlo k the frame 61 from the post 53₂.

(c) Reference is made to FIG. 5. The stem 84 of the valved probe assembly 80 remains in retracted position as in FIG. 4. Following penetration of the septum of vial 91 by the outer, rigid hollow needle 65 as occurs in (b), supra, downward movement of the frame 61 is continued. The locking action between the ball joints of the inertia lock mechanism which holds the two frames 51, 61 together is broken at the moment the lower base of frame comes into contact with the upper face of the probe seal assembly 80, after which moment the upper, or second frame 61 is telescoped with the lower, or first frame 51 of the injector feed assembly 60. As the frame 61 telescopes upon frame 51 the inner flexible bollow needle 66 is projected from within its position inside the outer rigid needle 65 to the outside of the outer rigid hollow needle 65, and extended to the very bottom of the vial 91 (FIG. 5). Because of the flexible nature of the hollow needle 66 neither the vial 91 or the needle 66 ar subject to damage albeit the terminal end of the needle 66 can bend and reach into the lowermost extremity of said vial 91.

(d) Continuing the reference to FIG. 5, pressurized gas is passed via line 67 into the tubular member 62 forming chamber 70, the gas passing therethrough through the annulus between the needles 65, 66 to pressurize the fluid contents of the vial 91. The pressurized fluid enters into the needle 66 passing upwardly therethrough to enter into the open valved end 13 of the syringe to fill the barrel of said syringe, or syringe assembly 10. When a preselected measured amount of the fluid specimen is trapped within the barrel 11, the valve 13 of the syringe is closed, the syringe 10 is moved downwardly via means not shown, the dispensing end of the needle 12 is thrust into the septum inlet 120 and an accurately measured amount of the fluid specimen contained within the barrel is ejected therein. The syringe 10 is then retracted to withdraw the needle 12 from the septum inlet, the valve 13 is opened, and the syringe 10 is again fully retracted to the position shown in FIG. 5.

(e) Reference is now again made to FIG. 4 which, taken in connection with FIG. 5 shows the reverse sequence. The frames 51, 61 are moved upwardly via actuation of the cylinder-piston unit 68 from the position described by reference to FIG. 5 to that shown by reference to FIG. 4. The inner flexible hollow needle 66 is thus withdrawn back into the protective outer rigid hollow needle 65, as frame 61 is again pushed upwardly. The frames 51, 61 are no longer telescoped.

(f) Continued reference is made to FIG. 4, which is compared with FIG. 3 to show the continued reverse sequence. Frames 51, 61 are thus pushed to their full extent upwardly, whereupon the hollow needles 65, 66 are likewise withdrawn upwardly to their full extent as depicted by reference to FIG. 3. A new vial, not shown, is then delivered by the magazine 90 to the station previously occupied by vial 91. The stem 84 is again extended to its extreme forward position. Thus, the valve 80 is again closed, the forward end of the valve stem 84 again physically blocking the opening 81.

(g) The purging, cleaning and drying step is described principally by reference to FIG. 3. The valved probe seal assembly 80 is closed, viz. the forward end of the stem 82 physically blocks the opening 81 of the valved probe seal assembly 80. In this position the lateral segment of the opening 92 is in open communication with opening 81, and the horizontal segment thereof is in open communication with conduit 1 to slop, or waste.

Referring first to FIGS. 2 and 2A, lines $67_1$, $67_2$ are each connected via a manifold (not shown) in block 75 to line 67. Each of lines $67_1$, $67_2$ are provided with a one-way check valve (not shown) so that air, or other fluid, will flow from line $67_1$ to 67 or from $67_2$ to 67, but not from line $67_1$ to $67_2$, or vice versa. Consequently, in a first step solvent is flowed via lines $67_1$, 67, and chamber 70 into the annulus between the probe needles 65, 66. Referring now to FIG. 3, solvent enters the opening 92, which is of slightly smaller diameter than the diameter of the annular opening, cleaning contaminant from the opening 81 and opening 92 whereupon it is passed via line 1 to slop. Solvent simultaneously passes up the inner flexible probe needle 66 to clean any contaminant therefrom, the solvent passing into the syringe 10 and then from the syringe 10 via the dispensing end of the needle 12 thereof. In a second drying step air is passed via line $67_2$, 67 to dry out the last traces of the solvent from the system, one portion of the air passing via opening 92 of stem 84 to slop, with the other passing via inner flexible probe needle 66 to the syringe 10.

It is apparent that various modifications and changes can be made without departing the spirit and scope of the present invention. The apparatus is constructed of materials substantially inert or nonreactive to the chemical or corrosive action of the fluid specimens to be measured and dispensed. The barrel of the fluid injector is normally constructed of glass, but can be constructed of a plastic or plastic-like material. The seals and tubing used in the instrument are normally constructed of rubber or plastic, and the rest of the instrument of various metals.

The seals are preferably formed of a rigid or semi-rigid, resilient form of plastic or plastic-like material. The self-lubricated plastics are especially preferred in this capacity, and can also be applied as a laminate or protective film. The polyfluorinated ethylene polymers, notable among which is polytetrafluoroethylene (Teflon), are particularly outstanding. Conventional resilient or plastic-like materials, such as natural or synthetic rubbers can also be employed.

The fluid injector sub-assembly (except for the barrel), the injector feed assembly, particularly the needle and probes, the piston units, and the like, are preferably constructed of metals, e.g., ferrous metals such as iron, iron alloys, steel, stainless steels, and the like; or such metals as aluminum, magnesium, brass, copper, bronze, chrome, alloys of these and other metals, and the like.

It is apparent that various changes, such as in the absolute or relative dimensions of the parts, materials used, and the like, as well as the suggested mode or particular sequence of withdrawing or delivering fluids, can be made without departing the spirit and scope of the invention, as will be apparent to those skilled in this art.

Having described the invention, what is claimed is:

1. In a fluid injector useful for the measurement and injection of preselected quantities of a fluid specimen into a medium such as an inlet to an analytical instrument wherein there is included the combination of (A) a syringe inclusive of a barrel into which a fluid specimen can be loaded, a needle mounted on an end of the barrel, and means for the displacement of the fluid specimen from said barrel via the dispensing end of the needle into said inlet, (B) an injector feed assembly comprises of a probe sub-assembly inclusive of a pair of concentrically mounted hollow needles for the pick up of said fluid specimen for filling the barrel of said syringe, and (C) a magazine for transporting one or more fluid specimen-containing septum sealed vials for pick up of fluid from a vial by the pair of hollow needles of said probe sub-assembly of said injector feed assembly for delivery to the barrel of said syringe via thrust of the hollow needles of said probe sub-assembly through the septem of a vial on pressurizing the contents of said vial by delivery of gas from a source through an annulus between the exterior surface of said inner hollow needle and the interior surface of said outer hollow needle of the pair of concentrically mounted hollow needles of said probe sub-assembly to produce flow of fluid specimen from said vial through the probe sub-assembly to the barrel of the syringe, the improvement wherein the pair of concentrically mounted hollow needles of said probe sub-assembly of the injector feed assembly (B) is comprised of the combination of (i) an outer rigid tubular needle of relatively large inside diameter, an end of which is directly affixed to said injector feed assembly, and (ii) an inner flexible tubular needle, a terminal end and at least an adjacent portion thereof of which is contained within the bore of said outer rigid tubular needle and is of sufficiently small outside diameter to form an annulus between the external surface of said inner flexible tubular needle and the internal surface of said outer rigid tubular needle, while the opposite end of said inner flexible tubular needle is communicated with the barrel of said syringe, whereby the outer rigid tubular needle protects the inner flexible needle when the pair of concentrically mounted hollow needles of the probe sub-assembly is thrust through the septum of a fluid specimen containing vial delivered by the magazine, and the inner flexible tubular needle can thereafter be thrust outside said outer rigid tubular needle and extended to the very bottom of a fluid specimen-containing vial such that on pressurization of the contents of the vial with a gas delivered via the annulus of the pair of concentrically mounted hollow needles of the probe sub-assembly essentially all of the fluid specimen can be removed from a vial, picked up by the probe sub-assembly, delivered to the barrel of the syringe, and injected into a medium via the dispensing end of the needle of the syringe.

2. The apparatus of claim 1 wherein the pair of concentric needles of the probe sub-assembly of the injector feed assembly (B) are mounted upon a pair of telescoping frames, a first frame provided with a base, an opening through said base, a plurality of shafts, spaced apart and parallelly oriented one with respect to the other supported upon said base, a second frame provided with a plurality of openings corresponding in number and orientation with the shafts on the base of said first frame within which said shafts of said first frame are guided and slidably mounted such that said second frame telescopes upon said first frame, a tubular barrel mounted and sealed within said second frame the central axis of which is aligned upon the central axis of the opening within the base of said first frame, a gas inlet to the tubular barrel, the outer rigid tubular needle of the pair of hollow needles of said probe sub-assembly being mounted, reciprocably movable, and sealed within said tubular barrel of said second frame, while the inner flexible tubular needle of the pair of needles is affixed to said second frame, passed through said tubular barrel and movable with said second frame such that it is reciprocably projectable into and out of the outer rigid hollow needle of the probe pair, the inner flexible tubular needle being shielded within the outer rigid tubular needle in an initial stage of movement in which said telescoping frames move together in unison to penetrate the septum of a specimen-containing vial by said outer needle, and thereafter in a second stage of movement the hollow flexible inner needle is projected outside said outer rigid hollow needle when the frames are telescoped and the hollow flexible inner needle extended to the lowermost portion of a fluid specimen-containing septum sealed vial delivered by the magazine for pick up of a fluid specimen therefrom for delivery to the syringe.

3. The apparatus of claim 2 wherein the injector feed assembly (B) further includes a probe seal assembly mounted between the said pair of telescoping frames and the magazine, the terminal end of the outer rigid hollow needle terminating within a lateral opening thereof within which it is sealed.

4. The apparatus of claim 3 wherein the probe seal assembly is valved, and contains an opening which intersects said lateral opening and within which a valve stem is mounted and in one position the end of the valve stem can be withdrawn from said lateral opening to permit passage therethrough of said outer rigid hollow needle, and in another position providing a means for purging, cleaning and drying said apparatus.

5. In a fluid injector useful for the measurement and injection of preselected quantities of a fluid specimen into a medium such as an inlet to an analytical instrument the combination comprising (A) a syringe inclusive of a barrel into which a fluid specimen can be loaded, a needle mounted on the forward end of the barrel, and means for the displacement of the fluid specimen from said barrel, via the dispensing end of the needle into said inlet, (B) an injector feed assembly inclusive of a probe sub-assembly which includes a pair of telescoping frames, a first frame provided with a base, an opening through said base, a plurality of shafts, spaced apart and parallelly oriented one with respect to the other supported upon said base, a second frame provided with a plurality of openings corresponding in number and orientation wtih the shafts on the base of said first frame within which said shafts of said first frame are guided and slidably mounted upon said first frame, locking means for locking together said first frame and said second frame so that said frames can be moved simultaneously, and unlocked such that said second frame can be telescoped upon said first frame, a tubular barrel mounted within and sealed inside said second frame the central axis of which is aligned upon the central axis of the opening within the base of said first frame, a gas inlet to the tubular barrel mounted and sealed within said second frame, a pair of concentrically mounted hollow needles, an outer rigid tubular needle of relatively large inside diameter mounted, reciprocably movable, and sealed within said tubular barrel of said second frame, an inner flexible tubular needle, a terminal end and at least an adjacent portion thereof which is contained within the opening through said outer rigid tubular needle, the inner flexible needle being affixed to said second frame and of sufficiently small outside diameter to form an annulus between the external surface of said inner flexible tubular needle and the internal surface of said outer rigid tubular needle, said annulus being communicated with the tubular barrel mounted within and sealed inside said second frame said with the gas inlet to said-tubular barrel, while the opposite end of said inner flexible tubular needle is communicated with the barrel of said syringe, (C) a magazine for transporting one or more fluid specimen-containing septum sealed vials for pick up therefrom of a fluid specimen by the injector feed probe sub-assembly when the second frame in a first stage is moved concurrently with said first frame to thrust the outer hollow rigid needle through the septum of said specimen sealed fluid specimen-containing vial, and in a second stage of movement the second frame is telescoped upon said first frame to thrust and extend the inner hollow flexible needle to the very bottom of said vial, gas injected via the gas inlet to the tubular barrel and passed via the annulus between the external surface of said inner tubular needle and the internal surface of said outer rigid tubular needle to pressurize the fluid-specimen within said vial such that essentially all of the fluid specimen within said vial can be conveyed via the iner flexible needle to the barrel of the syringe.

6. The apparatus of claim 5 wherein the fluid injector further includes a valved probe seal assembly adjacent said first frame of the injector feed assembly, said valved probe seal assembly comprising a valve body containing a first opening extending through said valve body in axial alignment with the opening in the base of said first frame and the septum of a septum sealed fluid specimen-containing vial transported therebeneath by the magazine, a second opening intersecting said first opening and extending through said valve body to a junction to which a drain line can be adjoined, a valve stem an end of which is provided with a opening constituted of axial and lateral segments, said stem being reciprocably mounted within said second opening, a first position of which the lateral portion of the stem opening can be aligned upon said first opening of the block and the axial stem portion of the opening with the second opening such that a gas, a cleaning solvent, and drying gas, can be serially injected via the annulus formed between said inner flexible needle and outer rigid needle of the injector feed assembly (B), to purge and clean said annulus, and eliminate contaminants by passage through said adjoined drain line, and purge and clean the inner flexible needle of the injector feed assembly (B), and syringe, and dry same, and a second position wherein the stem can be withdrawn so that the probe can be projected through said first opening into a fluid specimen-containing vial to effect pick up of fluid specimen from said vial carried by the magazine.

7. The apparatus of claim 6 wherein the valved probe seal assembly is generally cylindrical in shape, said first opening is a lateral opening through a forward end of the valve body of said probe seal assembly, said second opening extends along the axis of the cylindrical shaped valve body, the forward portion of said axial opening within the valve body is provided with a tubular nozzle to which the drain line for carrying a solvent and purge gas can be adjoined, the rearward end of the cylindrical shaped valve body carries an adjoining tubular shaped housing which carries the stem, the forward end of which is extended from said housing through said axial opening, the housing carrying a spring which biases the stem in position for cleaning, purging, and drying said fluid injector, and the position of the stem can be reset in an opposite position to carry out the function of loading the syringe with fluid specimen obtained from said vial.

8. The apparatus of claim 7 wherein the stem of the valved probe seal assembly is an integral portion of a cylinder-piston unit, the stem is spring-biased in a first position for cleaning, purging and drying said fluid injector, and pneumatically repositioned and reset to carry out the function of loading the syringe with fluid specimen obtained from said vial.

9. In a fluid injector useful for the measurement and injection of preselected quantities of a fluid specimen into a medium such as an inlet to an analytical instrument wherein there is included the combination of (A) a syringe inclusive of a barrel into which a fluid specimen can be loaded, a needle mounted on an end of the barrel, and means for the displacement of the fluid specimen from said barrel via the dispensing end of the needle into said inlet, (B) an injector feed assembly comprised of a probe sub-assembly inclusive of a pair of concentrically mounted hollow needles for the pick up of said fluid specimen for filling the barrel of said syringe, and (C) a magazine for transporting one or more fluid specimen-containing septum sealed vials for pick up of fluid from said vials by the pair of hollow needles of said probe sub-assembly by said injector feed assembly for delivery to the barrel of said syringe via thrust of the hollow needles of said probe sub-assembly through the septum of a vial, the contents of the vial pressurized by delivery of gas from a source through an annulus between the exterior surface of said inner hollow needle and the interior surface of said outer hollow needle of the pair of concentrically mounted hollow needles of said probe sub-assembly to produce flow of fluid specimen from said vial through the probe sub-assembly to the barrel of the syringe, the improvement wherein the pair of concentrically mounted hollow needles of said probe sub-assembly of the injector feed assembly (B) is comprised of the combination of (i) an outer rigid tubular needle of relatively large inside diameter, an end of which is directly affixed to said injector feed assembly, and (ii) an inner flexible tubular needle, a terminal end and at least an adjacent portion thereof of which is contained within the bore of said outer rigid tubular needle and is of sufficiently small outside diameter to form an annulus between the external surface of said inner flexible tubular needle and the internal surface of said outer rigid tubular needle, while the opposite end of said inner flexible tubular needle is communicated with the barrel of said syringe, (iii) a pair of telescoping frames, a first frame provided with a base, an opening through said base, a plurality of shafts, spaced apart and parallelly oriented one with respect to the other supported upon said base, a second frame provided with a plurality of openings corresponding in number and orientation with the shafts on the base of said first frame within which said shafts of said first frame are guided and slidably mounted, locking means for locking together said first frame and said second frame and for unlocking said first frame from said second frame such that said second frame can in a first stage be locked to said first frame and moved simultaneously therewith and, in a second stage unlocked from said first frame and telescoped upon said first frame, a tubular barrel mounted and sealed within said second frame the central axis of which is aligned upon the central axis of the opening within the base of said first frame, a gas inlet to the tubular barrel, the outer rigid tubular needle of the pair of hollow needles of said probe sub-assembly being mounted, reciprocably movable and sealed within said tubular barrel of said second frame, while the inner flexible tubular needle of the pair of needles, is affixed to said second frame, passed through said tubular barrel and movable with said second frame such that it is reciprocably projectable into and out of the outer rigid hollow needle of the probe pair, the inner flexible tubular needle being shielded within the outer rigid tubular needle whereby in said first stage of movement said frames are locked one to the other and moved together in unison, the inner flexible needle being transported within and shielded by the outer rigid needle of the concentric needles of the probe assembly to pentrate the septum of a specimen-containing vial by said outer needle, and thereafter in said second stage of continued movement the frames are unlocked one from the other and the second frame is telescoped upon said first frame so that the inner flexible needle is moved outside said outer rigid hollow needle and extended to the very bottom of said fluid specimen-containing vial such that on pressurization of the contents of the vial with a gas delivered via the annulus of the needles of the proble sub-assembly essentially all of the fluid specimen can be removed from said vial, picked up by the probe sub-assembly, delivered to the barrel of the syringe, and injected into a medium via the dispensing end of the needle of the syringe.

10. The apparatus of claim 9 wherein the pair of frames of the injector feed assembly are locked together via an inertia lock mechanism, unlocked, and telescoped on downward impact of a frame.

* * * * *